(12) United States Patent
Eberl et al.

(10) Patent No.: US 7,736,362 B2
(45) Date of Patent: Jun. 15, 2010

(54) CATHETER BALLOONS (75) Inventors: Gregory R. Eberl, Sunnyvale, CA (US); Mark D. Forrest, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1930 days.

(21) Appl. No.: 10/663,176

(22) Filed: Sep. 15, 2003

(65) Prior Publication Data
US 2005/0059965 A1 Mar. 17, 2005

(51) Int. Cl.
*A61B 18/18* (2006.01)
(52) U.S. Cl. ............................ 606/49; 606/41
(58) Field of Classification Search ............ 606/41–50, 606/194, 27–31; 607/96–107, 113
See application file for complete search history.

(56) References Cited

U.S. PATENT DOCUMENTS

| | | | |
|---|---|---|---|
| 4,643,186 A | 2/1987 | Rosen et al. | |
| 4,799,479 A | 1/1989 | Spears | |
| 4,979,948 A | 12/1990 | Geddes et al. | |
| 5,114,423 A | 5/1992 | Kasprzyk et al. | |
| 5,191,883 A | 3/1993 | Lennox et al. | |
| 5,236,413 A | 8/1993 | Feiring | |
| 5,318,531 A | 6/1994 | Leone | |
| 5,334,193 A | 8/1994 | Nardella | |
| 5,415,636 A * | 5/1995 | Forman ................. | 604/101.03 |
| 5,423,882 A | 6/1995 | Jackman et al. | |
| 5,462,545 A | 10/1995 | Wang et al. | |
| 5,505,730 A | 4/1996 | Edwards | |
| 5,522,873 A | 6/1996 | Jackman et al. | |
| 5,549,851 A | 8/1996 | Fukushima et al. | |
| 5,558,672 A | 9/1996 | Edwards et al. | |
| 5,562,720 A | 10/1996 | Stern et al. | |
| 5,569,241 A | 10/1996 | Edwards | |
| 5,738,901 A | 4/1998 | Wang et al. | |
| 5,769,880 A | 6/1998 | Truckai et al. | |
| 5,797,903 A | 8/1998 | Swanson et al. | |
| 5,840,076 A | 11/1998 | Swanson et al. | |
| 5,846,239 A | 12/1998 | Swanson et al. | |
| 5,860,974 A | 1/1999 | Abele | |
| 5,879,348 A | 3/1999 | Owens et al. | |

(Continued)

FOREIGN PATENT DOCUMENTS

EP 0768097 4/1997

(Continued)

OTHER PUBLICATIONS

PCT International Search Report for PCT/US2004/029059, Applicant: Scimed Life Systems, Inc., Forms PCT/ISA/210 and 220, dated Feb. 9, 2005 (6 pages).

(Continued)

*Primary Examiner*—Roy D Gibson
(74) *Attorney, Agent, or Firm*—Vista IP Law Group LLP (57) ABSTRACT

The present invention relates to catheter balloons wherein the balloon are constructed of hydrophilic energy conductive polymers. It also relates to catheter balloons that self-anchor at a target site in a patient's body. Finally, it relates to catheter balloons with very small cross-sectional profiles at the distal end.

26 Claims, 4 Drawing Sheets

U.S. PATENT DOCUMENTS

| | | | |
|---|---|---|---|
| 5,891,136 A | 4/1999 | McGee et al. | |
| 5,925,038 A | 7/1999 | Panescu et al. | |
| 5,961,513 A | 10/1999 | Swanson et al. | |
| 5,991,650 A | 11/1999 | Swanson et al. | |
| 5,997,532 A | 12/1999 | McLaughlin et al. | |
| 6,017,997 A * | 1/2000 | Snow et al. | 524/591 |
| 6,024,740 A | 2/2000 | Lesh et al. | |
| 6,032,077 A | 2/2000 | Pomeranz | |
| 6,071,278 A | 6/2000 | Panescu et al. | |
| 6,077,273 A * | 6/2000 | Euteneuer et al. | 606/108 |
| 6,080,151 A | 6/2000 | Swartz et al. | |
| 6,099,526 A | 8/2000 | Whayne et al. | |
| 6,117,101 A | 9/2000 | Diederich et al. | |
| 6,119,041 A | 9/2000 | Pomeranz et al. | |
| 6,123,718 A | 9/2000 | Tu et al. | |
| 6,241,666 B1 | 6/2001 | Pomeranz et al. | |
| 6,251,109 B1 | 6/2001 | Hassett et al. | |
| 6,254,599 B1 | 7/2001 | Lesh et al. | |
| 6,315,778 B1 * | 11/2001 | Gambale et al. | 606/41 |
| 6,416,511 B1 * | 7/2002 | Lesh et al. | 606/41 |
| 6,428,536 B2 | 8/2002 | Panescu et al. | |
| 6,475,213 B1 | 11/2002 | Whayne et al. | |
| 6,488,653 B1 * | 12/2002 | Lombardo | 604/103.06 |
| 6,488,658 B1 | 12/2002 | Long | |
| 6,488,688 B2 * | 12/2002 | Lim et al. | 606/108 |
| 6,500,174 B1 | 12/2002 | Maguire et al. | |
| 6,502,576 B1 | 1/2003 | Lesh | |
| 6,527,767 B2 | 3/2003 | Wang et al. | |
| 6,539,265 B2 | 3/2003 | Medhkour et al. | |
| 6,546,935 B2 | 4/2003 | Hooven | |
| 6,547,788 B1 * | 4/2003 | Maguire et al. | 606/41 |
| 6,605,087 B2 | 8/2003 | Swartz | |
| 6,732,735 B1 * | 5/2004 | Snell | 128/844 |
| 7,156,860 B2 * | 1/2007 | Wallsten | 606/192 |
| 2002/0082553 A1 | 6/2002 | Duchamp | |

FOREIGN PATENT DOCUMENTS

WO     WO 92/19290     11/1992

OTHER PUBLICATIONS

PCT Written Opinion of the International Search Authority for PCT/US2004/029059, Applicant: Scimed Life Systems, Inc., Form PCT/ISA/237, dated Feb. 9, 2005 (5 pages).

* cited by examiner

CATHETER BALLOONS

The present invention relates to medical devices, in particular to balloons for use with balloon catheters.

BACKGROUND OF THE INVENTION

Balloon catheters are used in many medical procedures such as ablation, drug delivery, brachytherapy, chemotherapy, coronary angioplasty and thromboembolectomy. Regardless of whether the use to which the balloon catheter is being put involves transmitting substances, as in the case of chemotherapy or brachytherapy, or transmitting energy, as in the case of ablation, to a target site, it is preferred that the transmitting surface of the balloon be maintained in close contact with the target surface. At present, this most often involves careful application and control of pressure to the balloon by the operator from a location quite remote from the balloon. This generally requires substantial skill and, depending on the length of the procedure being applied, can be quite exhausting.

Most balloon catheter uses require means for delivering a therapeutic payload (the most notable exception being coronary angioplasty wherein the expansion of the balloon itself elicits the desired therapeutic effect), be it radiation, a drug, cold, RF energy, etc., to the target site. For example, to ablate an area of a vessel in a patient's body, RF energy must be delivered from its source, usually outside the patient's body, to specific locations on the balloon that is situated at the target site. Means for achieving this include having thin conductive metal electrodes displayed in a desired pattern on the outer surface of the balloon and using the patient's body as the second electrode or ground. Alternatively, the balloon itself may be rendered energy-transmissive by doping the material from which it is made with a conductive metal or other conductive substance. A non-conductive mask is then applied to a surface of the conductive balloon to create the desired ablation pattern. Numerous other ways of creating ablation balloons are known in the art. All of them are generally relatively complicated to manufacture and tend to be quite expensive.

It would be desirable to have a catheter balloon capable of self-anchoring at a target site in a patient's body to relieve the operator of the duty and to provide consistent and even contact for the duration of a procedure. It would also be desirable to have a simpler, less expensive energy-transmitting balloon. The present invention provides catheter balloons that meet both these desired criteria.

SUMMARY OF THE INVENTION

Thus, one aspect of this invention is a balloon catheter comprising a distally-located inflatable balloon comprising an energy-conductive hydrophilic polymer having a tensile strength of at least 3000 psi, wherein the balloon is molded to inflate to specified equilibrium dimensions when subjected to about one atmosphere of internal pressure.

In an aspect of this invention, the hydrophilic polymer further has an elasticity that permits the balloon to inflate to dimensions greater than its equilibrium dimensions under more than one atmosphere of internal pressure without failing.

In an aspect of this invention, the balloon can be inflated to dimensions at least 50% greater than its equilibrium dimensions.

In an aspect of this invention, the hydrophilic polymer, when hydrated, comprises from 10 volume percent to about 40 volume percent water.

In an aspect of this invention, the hydrophilic polymer, when hydrated, comprises about 20% volume percent water.

In an aspect of this invention, the hydrophilic polymer comprises a conductive homopolymeric or co-polymeric thermoplastic polyurethane when hydrated with an electrolytic solution.

In an aspect of this invention, the balloon further comprising a non-conductive polymer mask adhered to a surface of the balloon to create a pattern of conductive and non-conductive areas wherein the non-conductive polymer has physical and chemical characteristics compatible with those of the hydrophilic polymer.

In an aspect of this invention, the non-conductive polymer comprises a non-conductive homopolymeric or co-polymeric thermoplastic polyurethane.

In an aspect of this invention, the conductive areas of the balloon have a wall thickness of from about 0.0005" to about 0.005".

An aspect of this invention is a balloon catheter wherein the balloon, when inflated under about one atmosphere of pressure or over-inflated with greater than one atmosphere of pressure, the balloon comprises a generally elongate member having a proximal end, a distal end, a first diameter at or near the proximal end, a second diameter at or near the distal end and a third diameter located between the first and second diameters, wherein the first and second diameters may be the same or different, the third diameter is less than both the first and second diameters; the first diameter is coupled to the third diameter by a distal-facing sloping surface; and, the second diameter is coupled to the third diameter by a proximal-facing sloping surface.

In an aspect of this invention, the second diameter is less than the first diameter.

In an aspect of this invention the distal-facing sloping surface comprises a therapeutic element.

In an aspect of this invention, the therapeutic element is selected from the group consisting of an RF energy transmitting element, a microwave energy transmitting element, an ultrasound energy transmitting element, a laser light energy transmitting element, a drug delivery element, a radiation energy delivery element, a cryogenic energy transmitting element and a cutting element.

In an aspect of this invention, the balloon comprises a an energy-conductive hydrophilic polymer having a tensile strength of at least 3000 psi.

In an aspect of this invention, the hydrophilic polymer, when hydrated, comprises from 10 volume percent to about 40 volume percent water.

In an aspect of this invention, the hydrophilic polymer, when hydrated, comprises about 20% volume percent water.

In an aspect of this invention, the hydrophilic polymer comprises a conductive homopolymeric or co-polymeric thermoplastic polyurethane when hydrated with an electrolytic solution.

In an aspect of this invention, the thermoplastic polyurethane is TECOPHILIC®.

In an aspect of this invention, balloon further comprises a non-conductive polymer mask adhered to its distal-facing surface to create a pattern of conductive and non-conductive areas wherein the non-conductive polymer has physical characteristics compatible with those of the hydrophilic polymer.

In an aspect of this invention, the non-conductive polymer is NeoRez 967®.

In an aspect of this invention the non-conductive polymer comprises a non-conductive homopolymeric or co-polymeric thermoplastic polyurethane.

In an aspect of this invention, the non-conductive polyurethane is TECOFLEX®.

In an aspect of this invention, the conductive areas of the balloon have a wall thickness of from about 0.0005" to about 0.005".

In an aspect of this invention, the balloon catheter comprising an ablation balloon catheter.

In an aspect of this invention the energy conducted is RF energy.

An aspect of this invention is an electrode assembly, comprising an elongate member; an inflatable member secured to the elongate member, the inflatable member having a proximal end, a distal end, a lumen extending therebetween, and a conductive region; and, an electrode carried by the elongate member, the electrode located within the lumen of the inflatable member and proximal to the conductive region of the inflatable member.

In an aspect of this invention, with regard to the electrode assembly, the inflatable member comprises an energy-conductive hydrophilic polymer having a tensile strength of at least 3000 psi.

In an aspect of this invention, with regard to the electrode assembly, the inflatable member is molded to inflate to specified equilibrium dimensions when subjected to about one atmosphere of internal pressure.

In an aspect of this invention, with electrode assembly further comprising a non-conductive polymer mask adhered to a surface of the inflatable member to create a pattern of non-conductive area wherein the non-conductive polymer has physical and chemical characteristics compatible with those of the hydrophilic polymer.

BRIEF DESCRIPTION OF THE DRAWINGS

FIG. 1 is a schematic representation of a balloon catheter.

DETAILED DESCRIPTION OF THE EMBODIMENTS

The balloons of this invention may be used with any balloon catheter of any design. A balloon catheter is shown generically in FIG. 1. It is understood that nothing in the figure is intended, nor is to be construed, to limit the scope of this invention in any manner whatsoever.

Figure 1A:
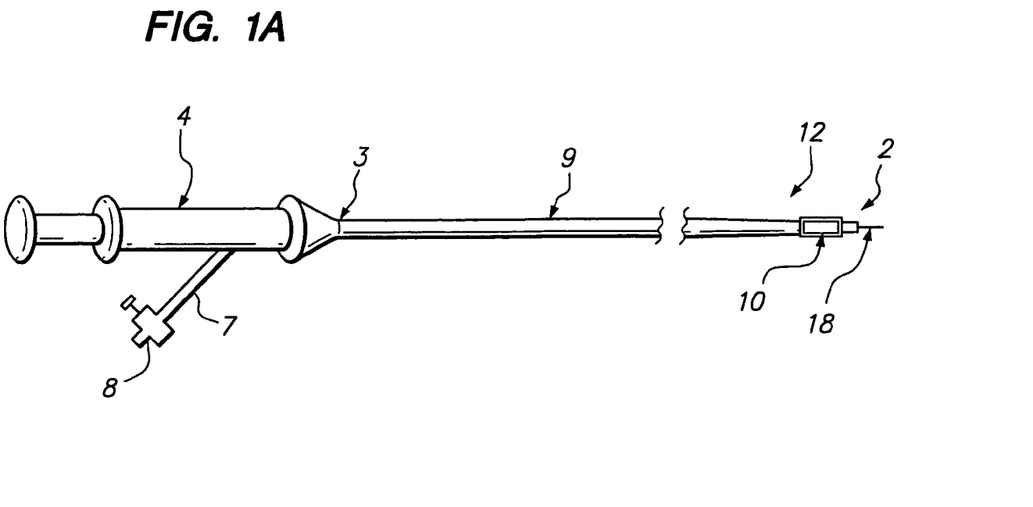
FIG. 1A shows the overall catheter and FIG. 1B shows a deployed balloon.
Figure 1B:
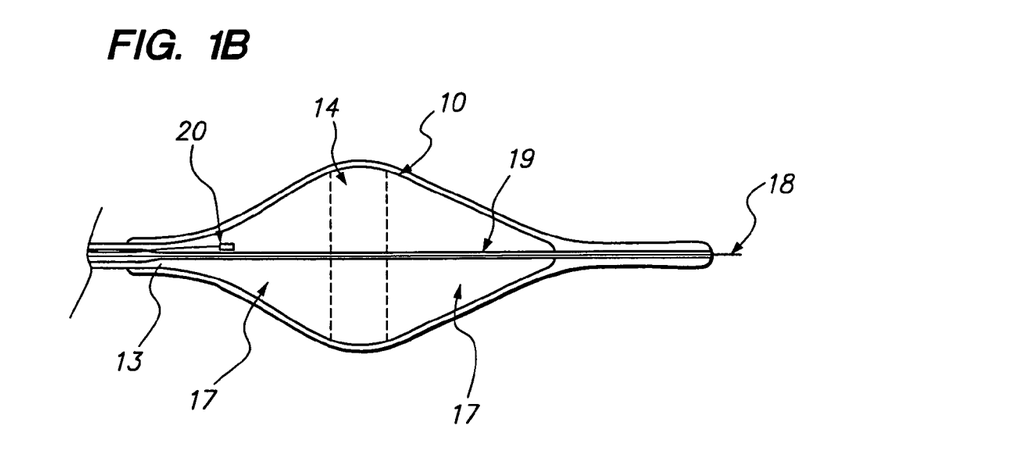

In FIG. 1A, catheter shaft 9 has a distal section 12 which contains deployable balloon 10, a shaft distal end 2 a shaft proximal end 3 and at least one lumen 13 extending between the two ends. Lumen 13 has at least one opening at the distal section 12 of the catheter shaft 9. Handle 4 is located at the proximal end of catheter shaft 9. The handle may contain means for controlling the movement of distal section 12 of shaft 9. Handle 4 may also include one or more hollow tubes 7, each having a proximal end, a distal end, a passageway and a locking valve 8 attached to it. Each such passageway is connected to one of the lumens 13 and is used to deliver and receive substances, in particular a working fluid for the inflation of the balloon when deployed, to and from distal section 12. In general, a balloon catheter has at least two lumens 13, one for inflation of the balloon and one for deflation of the balloon. In the case of an ablation balloon catheter, additional passageways and/or lumens are required for passage of wires from an RF generator, usually located remote from the catheter and connected thereto by electrical wires, to electrodes located at balloon 10. At the distal end of section 12 is a guide wire lumen 19 through which guide wire 18 is passed. FIG. 1B shows a balloon deployed and inflated. Balloon 10 is shown with a conductive region 14 and a non-conductive region 17, as would be the case when the balloon catheter is used for ablation. In this case, the working fluid used to inflate the balloon is usually physiological saline, which is conductive and compatible with body fluids. A ground electrode is attached to a remote location in the patient's body, conductive region 14 is placed in contact with tissue to be ablated and RF energy is transmitted to the saline by wire/electrode 20 which is attached to an energy source at its other end, and then through the conductive region 14 to the tissue. It is understood that depiction of the balloon as an ablation device is for illustrative purposes only and is not intended, nor is it to be construed, as limiting the invention in any way.

In one aspect of this invention, the balloon of the balloon catheter is constructed of a polymeric substance that is hydrophilic. By hydrophilic, it is meant that the polymer, when in contact with an aqueous solution, can absorb a quantity of water into it's structure while still maintaining its structural integrity. When the polymer absorbs water, it is said to be hydrated. To be useful as a balloon-forming material of this invention, the hydrophilic polymer must have sufficient strength to maintain structural integrity even when the balloon is subjected to substantial internal pressure as from a working fluid, usually physiological saline, used to inflate it and to external forces such as abrasion that might occur on contact with the interior surfaces of a patient's vessels. Thus, in a presently preferred embodiment of this invention, the hydrophilic polymer must have an ultimate tensile strength, both dry and in the hydrated state, of at least 3000 psi. As used herein, tensile strength has its usual meaning, that is, the force, measured in pounds per square inch (psi) needed to stretch the polymer until it breaks.

Balloons of this invention can be constructed by any of the various techniques well-known to those skilled in the art. For example without limitation, the polymer can be dip-coated on a mandrel that has a defined size and shape. When removed from the mandrel, the balloon, when inflated with about one atmosphere of pressure will assume the dimensions of the mandrel without incurring any tensional force in the polymer. The dimensions of a balloon inflated with about one atmosphere pressure after formation by whatever means selected will, for the purpose of this discussion, be called the balloon's equilibrium dimensions.

Balloons of this invention may also be formed by spin-coating in a hollow mold. When the mold is removed, as in the case of a dip-coated mandrel, the balloon will inflate to equilibrium dimensions that are the same as the interior dimensions of the hollow mold.

In addition, balloons can be formed by injection or blow molding. In this process, a pre-formed length of tubing made of the polymer is placed in a hollow mold having internal dimensions that reflect the desired equilibrium dimensions of the balloon to be formed. One end of the tube is sealed off and a working fluid is injected into the open end of the tube with sufficient force to cause the working fluid to expand the tubing until the wall of the tubing is in intimate contact with the inner surface of the mold. The polymer is then annealed, if desired, and cooled after which the mold is removed leaving a portion of the tubing as a balloon that, upon inflation, will assume equilibrium dimensions.

The above are but a few methods of forming balloons. Others will be apparent to those skilled in the art based on the disclosures herein. All such methods are within the scope of this invention.

In addition to tensile strength, in a presently preferred embodiment of this invention, the polymeric material of which a balloon is made has sufficient elasticity so as to be capable of stretching substantially beyond its equilibrium dimensions without failing; that is tearing or bursting, when subjected to internal pressures greater than one atmosphere. Classically, elasticity is a measure of the ability of a material to stretch under tension to beyond its initial dimensions and then to return to, or nearly to, its original dimensions when the tension is relaxed. While the polymers used to make the balloon of this invention may react in the classical manner and, as such, are within the scope of this invention, such is not necessarily the case. That is, a balloon of this invention may be capable of inflation up to 400% of its equilibrium dimensions but may not return to, or even nearly to, its equilibrium dimensions when deflated and may in fact remain substantially "stretched out." It is presently preferred that the hydrophilic polymer selected for balloons of this invention be such that the balloon is capable, when hydrated, of up to 50% expansion beyond its equilibrium dimensions. When being inflated, a balloon of this invention will expand in such a manner that all its dimensions increase in approximately a constant ratio to the corresponding equilibrium dimension; that is, as it is inflated the balloon essentially retains its initial equilibrium shape—it just gets bigger.

A presently preferred hydrophilic polymer from which to make balloons of this invention is TECOPHILIC®, manufactured by Thermedics Polymer Products, Woburn, Mass. TECOPHILIC® is a polyether-based aliphatic polyurethane. The TECOPHILIC® family of polyurethanes meet all the criteria discussed above for balloon of this invention. That is, TECOPHILIC® HP-60D-35, a presently preferred member of the family from which to manufacture balloons of this invention, has an ultimate tensile strength (pressure required to break apart a sample of polymer) of 7800 psi dry and 4900 hydrated. In addition, it has an ultimate elongation, i.e., elongation to break which is related to elasticity as used herein, of 450% dry and 390% hydrated. Other hydrophilic polymers having the desired physical characteristics will become apparent to those skilled in the art based on the disclosures herein and are within the scope of this invention.

The TECOPHILIC® balloon is rendered conductive by hydration with an electrolytic solution, that is, a solution containing sufficient ionic content to conduct energy such as, in a presently preferred embodiment, RF energy. For medical use, the electrolytic solution is normally physiological saline, that is, a sterile approximately 0.9% aqueous sodium chloride solution that is isotonic with body fluids. Any salt solution at any desired concentration can, however, be used although it is preferred that the salt be one that is not detrimental to tissue or the health of the patient in the unlikely event that a balloon should inadvertently rupture.

Figure 2:
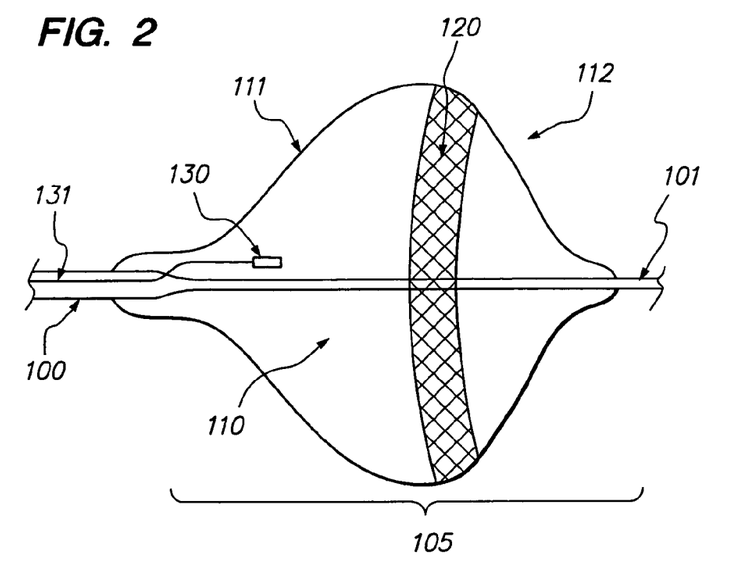
FIG. 2 is a schematic representation of a balloon of this invention shown in the form of an ablation balloon. The depiction of an ablation balloon, while an aspect of this invention, is not the only use to which the balloons herein can be put. That is, the depiction is for illustrative purposes only and is not intended, nor should it be construed as limiting the scope of this invention.

In another aspect, a balloon of this invention is intended for use in an ablation balloon catheter. For this use, a non-conductive mask is applied to a surface of the conductive hydrophilic balloon to create a pattern for ablation. Such a masked balloon is shown in FIG. 2. Balloon 105 has distal-facing surface 112 and proximal-facing surface 111. Proximal catheter shaft 100 protrudes from the proximal end of balloon 105 while catheter tip 101 protrudes from the distal end of balloon 105. The non-cross-hatched portions 110 of the surface of balloon 105 are non-conductive by virtue of a mask adhered to a surface of the balloon. The mask may be adhered to the outer or inner surface of the balloon. Cross-hatched portion 120 of the surface of balloon 105 is the conductive region. When the distal end of balloon 105 is inserted in a vessel such as the pulmonary vein of a patient from within the heart, region 120 is pressed up against the heart wall at the ostium or opening from the heart into the vein. A ground electrode is attached to a remote location on the patients body and then an RF signal is generated at the proximal end of the catheter proximal to section 100 of the catheter shaft (usually at a generator attached to the catheter in the vicinity of the handle) and is transmitted through wire 131 to electrode 130. The signal is conducted through region 120 of the balloon and a circuit is completed so that RF energy is delivered to the tissue in contact with region 120 and is thereby ablated.

In order for a masked balloon of this invention to operate properly, the non-conductive polymer used to create the mask must have physical characteristics compatible with those of the hydrophilic polymer used to form the balloon. That is, at the very least, the non-conductive polymer must have a tensile strength and elasticity at least equivalent to that of the hydrophilic polymer so that the non-conductive polymer does not prematurely break when the balloon is inflated thus disrupting the desired ablation pattern. It is also necessary that the non-conductive polymer have chemical characteristics compatible with those of the hydrophilic polymer, at least insofar as is necessary to achieve sufficient adhesion of the non-conductive mask to the surface of the hydrophilic polymer balloon both in the dry and hydrated state. Sufficient adhesion means that the mask will remain in place and will not separate from the surface of the balloon either when the balloon is deflated, folded and stored in the catheter or when the balloon is deployed, hydrated and inflated.

A wide range of non-conductive polymers can be used to create masks compatible with a TECOPHILIC® balloon. For example, without limitation, when the TECOPHILIC® balloon is formed by the dip-molding method, a presently preferred mask polymer is TECOFLEX® SG-85A, also manufactured by Thermedics Polymer Products. TECOFLEX®, like TECOPHILIC®, is a polyether-based aliphatic polyurethane and therefore is very compatible with TECOPHILIC® chemically so that masks formed from TECOFLEX® adhere well to surfaces made of TECOPHILIC®. In addition, the TECOFLEX has an ultimate tensile strength and elongation that is compatible with the TECOPHILIC. Other matching TECOFLEX® and TECOPHILIC® family members useful for making the balloons of this invention will become apparent to those skilled in the art based on the disclosure herein and are within the scope of this invention.

When the TECOPHILIC® balloon is made by a blow-molding procedure, the presently preferred masking polymers are those that can be coated from an aqueous medium so as to avoid contacting the TECOPHILIC® with a solvent that might affect its integrity. An example, without limitation, of such a non-conductive masking polymer is NeoRez 967® from NeoResins, Wilmington Del. Of course, aqueous medium polymers may also be used with TECOPHILIC® balloons made by any method, not just blow-molded balloons so that, for example without limitation, NeoRez 967® could be substituted for TECOFLEX® in the above-described dip-coated balloon.

If desired, the surface of the TECOPHILIC® balloon can be pre-treated to assist in prevention of bead formation during film formation and to enhance adhesion and coating uniformity. For example, without limitation, the surface of the TECOPHILIC® balloon can be subjected to an Argon plasma prior to coating.

Based on the disclosures herein, other hydrophilic polymers that can be rendered conductive by hydration with electrolytic solutions and that have the requisite physical characteristics, other non-conductive polymers that are chemically and physically compatible with the hydrophilic polymer and other means of treatment of surfaces to enhance adhesion of the non-conductive mask polymer will become apparent to, or will be readily determinable without undue experimentation by, a skilled artisan. All such polymers and combinations of polymers are within the scope of this invention.

In ablation therapy and in many other balloon catheter applications such as those mentioned in the Background section of this application, it is desirable, often necessary, to maintain the surface of the balloon that comprises the therapeutic element in intimate contact with a patient's tissue. As used herein, a "therapeutic element" simply refers to the features of that portion of a balloon that permits the desired therapy to be administered. For example, without limitation, for ablation therapy the therapeutic element is the conductive portion of the balloon that is in contact with the tissue to be ablated. For the administration of drugs, that portion of the balloon that is in contact with the patient's tissue must be permeable to the drug. Similarly, for brachytherapy, the portion of the balloon that is in contact with the tissue to be treated must be capable of retaining the radioactive material on its surface and then controllably depositing it at the target site. To maintain intimate contact of the therapeutic element of the balloon with the target tissue, a means for self-anchoring of the balloon in the correct orientation would be highly desirable. This can be accomplished using the essentially hourglass-shaped balloon of this invention shown in FIG. 3.

Figure 3:
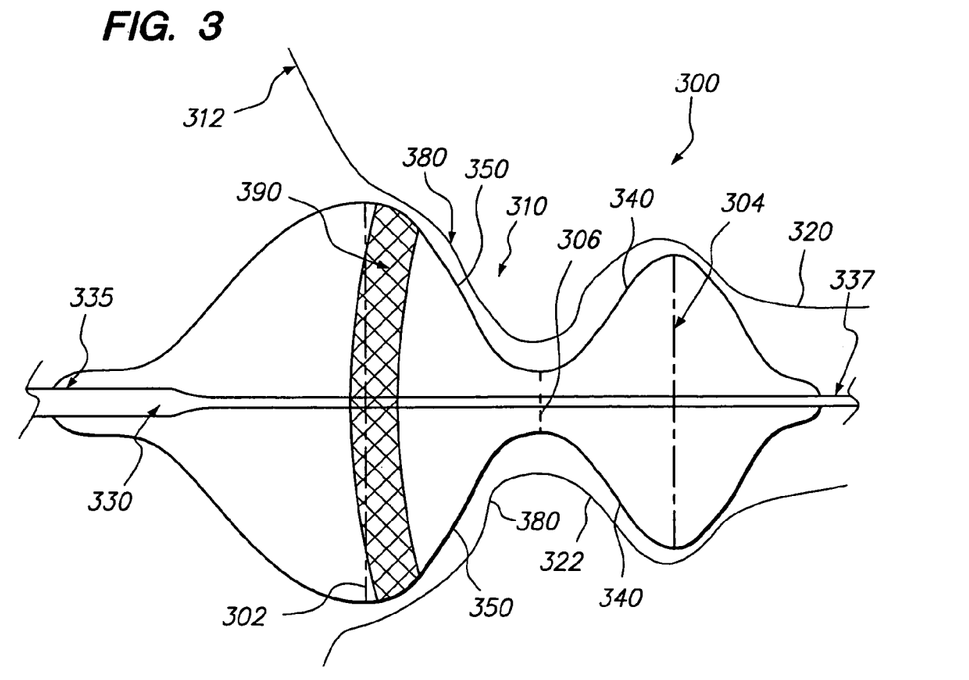
FIG. 3 is a schematic representation of a self-anchoring balloon of this invention. Again, the balloon is shown as an ablation balloon but this is for illustrative purposes only and likewise is not intended, nor is it to be construed as limiting the scope of this invention in any manner whatsoever.

In FIG. 3, balloon 300 is shown inflated in the locus of the ostium 310 of a vessel 320 in a patient's body. Balloon 300 consists of a first diameter 302, a second diameter 304 and a third diameter 306. Diameter 306 is smaller than either diameter 302 or diameter 304. Diameters 302 and 304, on the other hand, can be the same or different. In a presently preferred embodiment of this invention diameter 304 is less than diameter 302 (and diameter 306 is less than either of the other two). The catheter shaft 330, having distal end 335 and proximal end 337 is inserted into the vessel prior to inflation of the balloon. As the balloon inflates, the segment having diameter 304 expands and presses against wall 322 of vessel 320, causing it to dilate. The tissue 380 at the proximal side of the ostium is, in most circumstances, thicker than and therefore less elastic than the tissue of the wall 322 of the vessel. Thus, as the portion of balloon 300 having diameter 304 is increased by inflation of the balloon, the pressure of proximal-facing sloped surface 340 against wall 322 pulls distal-facing sloped surface 350 into intimate contact with tissue 380 in the vicinity of the ostium and holds it there thus relieving the operator of the chore of manually maintaining pressure on the balloon. This is at times referred to herein as self-anchoring of the balloon.

For the purpose of illustration only, the balloon is shown as an ablation balloon. That is, the distal-facing sloped surface 350 is shown as having an energy-conductive band 380 that contacts tissue around the ostium. The remainder of the balloon is masked by a non-conductive polymer. Upon delivery of RF energy to the energy conductive region of the balloon, the contacted tissue is ablated. It is understood, however, that region 390 or, in fact, any or all portions of distal-facing sloped surface 350 that is in intimate contact with tissue may constitute a therapeutic element. That is, a drug could be diffused through surface 350 and infused into the tissue, and radioactive beads could be removably adhered to surface 350 and transferred to the tissue, etc. In all these applications, the segment of the balloon having diameter 304 maintains the contact necessary to obtain the desired effect.

Figure 4:
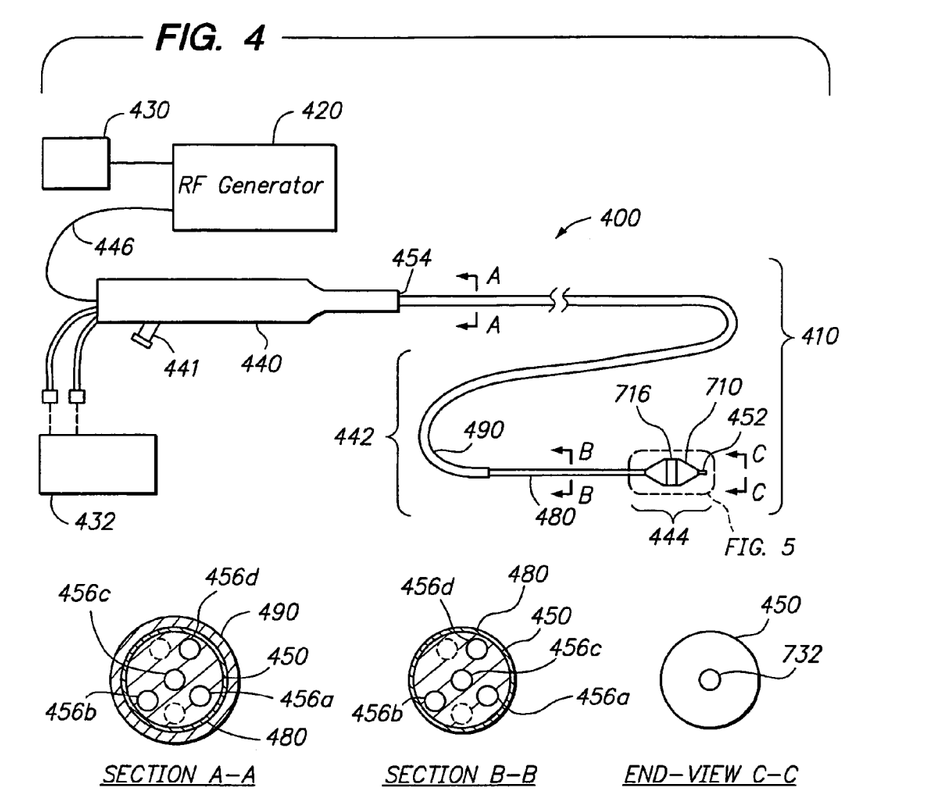
FIG. 4 is a schematic representation of an ablation system, which includes a balloon in accordance with an embodiment of this invention. The depiction of an ablation balloon, while an aspect of this invention, is not the only use to which the balloons herein can be put. That is, the depiction is for illustrative purposes only and is not intended, nor should it be construed as limiting the scope of this invention.

FIG. 4 shows a tissue ablation system 400, which includes a balloon constructed in accordance with an embodiment of the present invention. The system 400 includes an ablation catheter 410, a generator 420 for delivering energy to the catheter 410 to ablate tissue, an indifference electrode 430 (e.g., an electrode pad) coupled to the generator 420, and a source 432 of fluid coupled to the catheter 410. The catheter 410 comprises a handle assembly 440, a guide tube assembly 442, and an electrode assembly 444 having an inflatable balloon 710. During use, the guide tube assembly 442 delivers electrically conductive fluid from the fluid source 432 to inflate the balloon 710 at the electrode assembly 444.

The generator 420 is coupled to the handle assembly 440 of the catheter 410 via a cable 446, so that radio frequency (RF) energy can be delivered to the electrode assembly 444. In the illustrated embodiment, the system 400 operates in a unipolar mode. In this arrangement, during use, the indifference electrode 430 is attached to a patient's back or other exterior skin area, and ablation energy will flow from the electrode assembly 444 to the patch electrode 430. Alternatively, the system 400 can be operated in a bipolar mode, in which case, the system 400 does not include the indifference electrode 430, and ablation energy will flow from one electrode on the electrode assembly 444 to an adjacent electrode (not shown) on the electrode assembly 444 or on the guide tube assembly 442.

Figure 5:
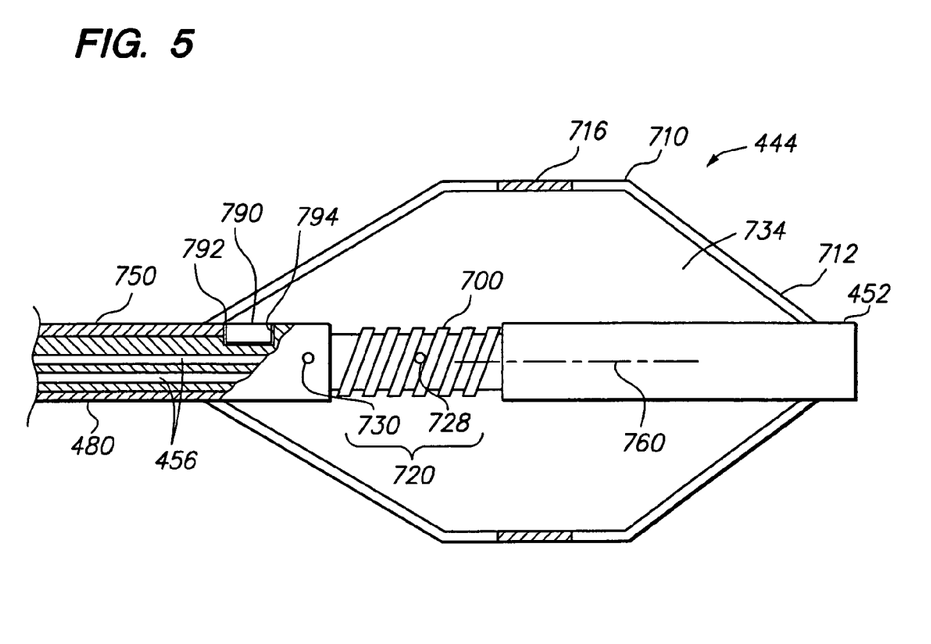
FIG. 5 illustrates a side cross sectional view of an electrode assembly, which includes a balloon in accordance with an embodiment of this invention.

The guide tube assembly 442 includes an inner shaft 450 having a distal end 452, a proximal end 454, and a plurality of lumens 456 extending therebetween. As shown in FIG. 5, the shaft 450 also includes an inflation port 728 and a deflation port 730 located along the shaft 450, and a distal opening 732 at the distal tip of the shaft 450. In the illustrated embodiment, the shaft 450 includes four lumens 456a-456d. Lumen 456a, which is in fluid communication with the inflation port 728, is used to deliver fluid from the fluid source 432 to the electrode assembly 444 for inflation of the balloon 710. Lumen 456b, which is in fluid communication with the deflation port 730, is used to transport delivered fluid from the electrode assembly 444 back to the fluid source 432 or to another container for disposal of the fluid as the balloon 710 is deflated. Lumen 456c extends to the distal tip opening 732, and can be used to house a guidewire (not shown) that is inserted into the opening 732, through the shaft 450, and out of a port 441 located on the handle assembly 440. Lumen 456d is used to house wire(s) (e.g., RF lead wires and thermistor wires) that connect an electrically activated element at the electrode assembly 444 to the generator 420. It should be noted that the size and shape of the lumens 456 should not be limited to the example illustrated in the figure, and that the lumens 456 can have sizes and shapes that are different from that shown. In addition, the functionalities of the lumens 456 can vary. For example, in another embodiment, lumen 456c can be used to deliver radiopaque contrast to a target site. In the illustrated embodiment, the inner shaft 450 comprises a lower durometer Pebax braided shaft. However, the inner shaft 450 can also be made from a variety of materials, such as polymer, plastics, a thermoplastic material (e.g., plyurethane, polyolefin or polyetherpolyamide block copolymer).

As shown in FIGS. 4 and 5, the guide tube assembly 442 also includes an outer shaft 480 coaxially surrounding the inner shaft 450 to strengthen and/or to improve a durability of the guide tube assembly 442, and an outer sheathing 490 secured to an outer surface of the outer shaft 480 for enhancing a stiffness of the guide tube assembly 442. Materials suitable for construction of the inner shaft 450 can also be used for the outer shaft 480. The diameter or the cross sectional dimension of the outer shaft 480 is preferably about 5.5 French (F). However, the outer shaft 480 can also have other cross sectional dimensions. The sheathing 490 can include, for example, a stainless steel coiled into a flexible spring, and a sheath of extruded plastic material containing wire braids enclosing the spring. Such construction provides additional torsional stiffness to the shaft 450, thereby allowing a torquing force to be transmitted from the handle assembly 440 to the electrode assembly 444 of the catheter 410. In the illustrated embodiment, the outer sheathing 490 does not extend completely to the distal end of the catheter 410. Alternatively, the outer sheathing 490 can extend to a proximal end of the electrode assembly 444 or to the distal end 452 of the inner shaft 450.

The electrode assembly 444 will now be described with reference to FIG. 5. The electrode assembly 444 includes an electrode 700 secured to the guide tube assembly 442, and a balloon 710. The balloon 710 has a distal end 712 and a proximal end 714 secured to the guide tube assembly 442. The balloon 710 also has a conductive region 716 located between the distal and proximal ends 712, 714. In the illustrated embodiment, the electrode 700 is a coil having a lumen that extends between the ends of the coil. Ablation wires (not shown) connect the electrode 700 to the generator 420, and are housed in one of the lumens 456 of the shaft 450. The electrode 700 is secured to the shaft 450 by a suitable adhesive at both ends of the electrode 700. Alternatively, the electrode 700 can be secured to the shaft 450 at other locations of the electrode 700. Using a coil for construction of the electrode 700 is advantageous in that it allows the shaft 450 to easily deflect or bend as the shaft 450 is delivered over a guidewire. The coil electrode 700 also provides a large electrode surface to improve heat dissipation and lower impedance during use. The shaft 450 has a section 720 with a diameter or cross sectional dimension that is less than that of an adjacent section of the shaft 450, such that when the electrode coil 700 is placed around the section 720, the electrode 700 will substantially flush with an exterior surface of the outer shaft 480 to form a smooth surface. Such configuration reduces the overall profile of the electrode assembly 444, and reduces the risk of the electrode 700 abrading the balloon 710 during use.

In the illustrated embodiment, the electrode 700 is positioned proximal to the conductive region 716 of the balloon 710. Such configuration prevents the electrode 700 from abrading the conductive region 716 of the balloon 710 during use (e.g., while inserting the balloon 710 into a delivery or access tube), and allows the electrode assembly 444 to form more uniform lesions without excessive charring. Alternatively, the electrode 700 can be placed distal to the conductive region 716, or at the same axial location along an axis 760 of the inner shaft 750.

It should be noted that the configurations of the electrode 700 and the balloon 710 are not limited to those shown in the figure. In alternative embodiments, the electrode 700 can have a shape of a ring, a tubular segment, or other shapes, and the balloon 710 can have other shapes, such as a spherical shape, an elliptical shape, or a dumbbell shape. In addition, instead of extending through the balloon 710, in an alternative embodiment, the distal end 452 of the shaft 450 does not penetrate through the balloon 710. Instead, the balloon 710 has a closed distal end 712, and the electrode 700 is secured to the distal end 452 of the shaft 450, which is disposed within a lumen 734 of the balloon 710. In such case, the distal end 452 of the shaft 500 has one or more openings that are in fluid communication with the one or more lumens 456 of the shaft 450 for delivering and draining fluid to and from the lumen 734 of the balloon 710. Alternatively, the distal end 452 of the shaft 450 has a closed tip, in which case, the shaft 450 has one or more openings 728 along its length for delivering and draining inflation fluid to and from the balloon 710, as similarly discussed previously. Furthermore, instead of securing to the shaft 450, the electrode 700 can be secured to a distal end of an elongate structure, such as a pusher, which is slidably disposed within one of the lumens 456 of the shaft 450. Such configuration allows a position of the electrode 700 along the axis 760 of the shaft 450 be adjusted during use.

As shown in FIG. 5, the electrode assembly 444 also includes a sensor 790, such as a thermistor, secured to the inner shaft 450. The outer shaft 480 has an opening 792 and the inner shaft 450 has a recess 794 for accommodating the sensor 790. The recess 794 has a depth such that when the sensor 790 is attached to the inner shaft 450, the sensor 790 lies substantially flush with an exterior surface of the outer shaft 480. It should be noted that the sensor 790 is not necessarily limited to a thermistor, and that the sensor 790 can be a variety of sensing devices, such as an impedance sensor or a current sensor.

A method of using the system 400 will now be described with reference to cardiac ablation therapy. When using the system 400 for cardiac ablation therapy, a physician inserts a guidewire through a main vein or artery (typically the femoral vein or artery) of a patient into an interior region of a heart that is to be treated. The physician then inserts a proximal end of the guidewire into the distal opening 732 of the inner shaft 750, and distally advances the electrode assembly 444 over the guidewire until the electrode assembly 444 reaches a treatment site. In one embodiment, an access shaft or tube can be provided and inserted over the guidewire. In such case, the electrode assembly 444 can be placed in the access shaft and distally advanced to reach the treatment site. Alternatively, the electrode assembly 444 can be placed within the access shaft first, and the electrode assembly 444 together with the access shaft are then delivered over the guidewire, and advanced to the treatment site. In another embodiment, the catheter 410 can include a steering mechanism for steering a distal end of the catheter 410. In such case, the use of the guidewire and/or the access shaft may not be required, and the physician can place the electrode assembly 444 into contact with a tissue within the heart that is targeted for ablation by operating the steering mechanism. When the electrode assembly 444 is desirably positioned, inflation fluid, such as an electrically conductive fluid, is then delivered from the fluid source 432 to the electrode assembly 444. Particularly, the fluid exits through inflation port 728 to inflate the balloon 710. Energy is then directed from the generator 420 to the electrode 700, and energy will flow from the electrode 700 to the conductive region 716 via the delivered conductive fluid to ablate the tissue and form a lesion on the tissue. When a desired lesion has been created, the delivered fluid can be drained from the lumen 734 of the balloon 710 to deflate the balloon 710, and the catheter 410 can be removed from the patient.

Based on the disclosures herein those skilled in the art will recognize many changes that might be incorporated in the materials used to make the balloons of this invention, the shape of the balloons to provide self-anchoring and the features of the small cross-section balloon catheter. Likewise, different embodiments and applications of the inventions disclosed herein with also be recognized by those skilled in the art based on the disclosures herein. All such changes, embodiments and applications are within the scope of this invention.

What is claimed:

1. A medical probe, comprising:
   an elongate shaft; and
   an inflatable balloon distally located on the elongate shaft, the inflatable balloon comprising a hydrophilic polymer being electrically conductive and having a tensile strength of at least 3000 psi when hydrated with an electrolytic solution, wherein the balloon is configured to inflate to specified equilibrium dimensions when subjected to about one atmosphere of internal pressure; and
   an electrically non-conductive polymer mask adhered to a surface of the balloon to create a pattern of electrically conductive and electrically non-conductive areas when the hydrophilic polymer is hydrated with the electrolytic solution, wherein the electrically non-conductive polymer has physical and chemical characteristics compatible with those of the hydrophilic polymer.

2. The medical probe of claim 1, wherein the inflatable balloon is an ablation balloon.

3. The medical probe of claim 2, wherein the electrically conductive areas of the balloon have a wall thickness of from about 0.0005" to about 0.005".

4. The medical probe of claim 1, wherein the hydrophilic polymer has an elasticity that permits the balloon to inflate to dimensions greater than its equilibrium dimensions under more than one atmosphere of internal pressure without failing.

5. The medical probe of claim 4, wherein the balloon can be inflated to dimensions at least 50% greater than its equilibrium dimensions.

6. The medical probe of claim 1, wherein the hydrophilic polymer, when hydrated, comprises from 10 volume percent to about 40 volume percent water.

7. The medical probe of claim 6, wherein the hydrophilic polymer, when hydrated, comprises about 20% volume percent water.

8. The medical probe of claim 1, wherein the electrically non-conductive polymer comprises an electrically non-conductive homopolymeric or co-polymeric thermoplastic polyurethane.

9. The medical probe of claim 8, wherein the electrically non-conductive polyurethane is a polyether-based aliphatic polyurethane.

10. The medical probe of claim 1, wherein the electrically non-conductive polymer is an aliphatic urethane.

11. A medical probe comprising:
    an elongate shaft;
    an inflatable balloon distally located on the elongate shaft, the balloon having a first diameter, a second diameter, and a third diameter located between the first and second diameters, wherein the third diameter is less than both the first and second diameters, the first diameter is coupled to the third diameter by a distal-facing sloping surface, and the second diameter is coupled to the third diameter by a proximal-facing sloping surface;
    an electrically non-conductive polymer mask adhered to the distal-facing surface of the balloon to create a pattern of electrically conductive and electrically non-conductive areas when the hydrophilic polymer is hydrated with the electrolytic solution, wherein the electrically non-conductive polymer has physical characteristics compatible with those of the hydrophilic polymer; and
    a therapeutic element located on the distal-facing sloping surface.

12. The medical probe of claim 11, wherein the electrically non-conductive polymer comprises an electrically non-conductive homopolymeric or co-polymeric thermoplastic polyurethane.

13. The medical probe of claim 12, wherein the electrically non-conductive polyurethane is a polyether-based aliphatic polyurethane.

14. The medical probe of claim 11, wherein the electrically non-conductive polymer is an aliphatic urethane.

15. The medical probe of claim 11, wherein the electrically conductive areas of the balloon have a wall thickness of from about 0.0005" to about 0.005".

16. The medical probe of claim 11, wherein the balloon is an ablation balloon.

17. The medical probe of claim 8, or claim 11, wherein the balloon is an RF ablation balloon.

18. The medical probe of any of claim 11 or claim 20, wherein the elongate shaft is configured to be intravascularly introduced into a patient.

19. The medical probe of claim 18, wherein the elongated shaft is configured to be introduced within a heart of the patient.

20. A medical probe, comprising:
    an elongate shaft;
    an inflatable member distally located on the elongate shaft, the inflatable member having a proximal end, a distal end, a lumen extending therebetween, and an electrically conductive region; and
    an electrode carried by the elongate member, the electrode configured for being in direct electrical contact with electrically conductive fluid within the inflatable member, the electrode located within the lumen of the inflatable member and proximal to the electrically conductive region of the inflatable member.

21. The medical probe of claim 20, wherein the inflatable member comprises hydrophilic polymer being electrically conductive and having a tensile strength of at least 3000 psi when hydrated within an electrolytic solution.

22. The medical probe of claim 21, wherein the hydrophilic polymer comprises a homopolymeric or co-polymeric thermoplastic polyurethane when hydrated with the electrolytic solution.

23. The medical probe of claim 22, wherein the thermoplastic polyurethane is a polyether-based aliphatic polyurethane.

24. The medical probe of claim 21, further comprising an electrically non-conductive polymer mask adhered to a surface of the inflatable member to create a pattern of electrically conductive and electrically non-conductive areas when the hydrophilic polymer is hydrated with the electrolytic solution, wherein the electrically non-conductive polymer has physical and chemical characteristics compatible with those of the hydrophilic polymer.

25. The medical probe of claim 20, wherein the inflatable member is configured to inflate to specified equilibrium dimensions when subjected to about one atmosphere of internal pressure.

26. A method of treating an ostium of a blood vessel, comprising:

inserting the medical probe of claim 11 through the ostium into the blood vessel;

inflating the balloon, so that expansion of the second diameter dilates the blood vessel, thereby causing a wall of the blood vessel to apply pressure to the proximal-facing sloped surface and to pull the distal-facing sloped surface into intimate contact with tissue in the vicinity of the ostium; and operating the therapeutic element to provide therapy to the ostium.

* * * * *